US00PP28599P2

(12) United States Plant Patent
Volmary

(10) Patent No.: US PP28,599 P2
(45) Date of Patent: Nov. 7, 2017

(54) ***LANTANA* PLANT NAMED 'VOLLAN 1317'**

(50) Latin Name: *Lantana camara*
Varietal Denomination: VOLLAN 1317

(71) Applicant: Hubertus Volmary, Muenster (DE)

(72) Inventor: Hubertus Volmary, Muenster (DE)

(73) Assignee: Volmary GmbH, Muenster (DE)

( * ) Notice: Subject to any disclaimer, the term of this patent is extended or adjusted under 35 U.S.C. 154(b) by 4 days.

(21) Appl. No.: 14/999,188

(22) Filed: Apr. 8, 2016

(51) Int. Cl.
*A01H 5/02* (2006.01)

(52) U.S. Cl.
USPC ..... Plt./227

(58) Field of Classification Search
USPC ..... Plt./227
See application file for complete search history.

*Primary Examiner* — Keith Robinson
(74) *Attorney, Agent, or Firm* — C. A. Whealy

(57) ABSTRACT

A new and distinct cultivar of *Lantana* plant named 'VOLLAN 1317', characterized by its compact, upright to outwardly spreading plant habit; freely branching growth habit; dense and bushy plant form; early and freely flowering habit; flowers that are initially yellow in color and with development become orange and red in color; and good garden performance.

1 Drawing Sheet

Botanical designation: *Lantana camara.*
Cultivar denomination: 'VOLLAN 1317'.

BACKGROUND OF THE INVENTION

The present invention relates to a new and distinct cultivar of *Lantana* plant, botanically known as *Lantana camara* and hereinafter referred to by the name 'VOLLAN 1317'.

The new *Lantana* plant is a product of a planned breeding program conducted by the Inventor in Muenster, Germany. The objective of the breeding program is to create new freely-branching *Lantana* plants with early and freely flowering habit and attractive flower coloration.

The new *Lantana* plant originated from an open-pollination in 2010 in Muenster, Germany of an unnamed proprietary selection of *Lantana camara*, not patented, as the female, or seed, parent with an unknown selection of *Lantana camara* as the male, or pollen, parent. The new *Lantana* plant was discovered and selected by the Inventor as a single flowering plant from within the progeny of the stated open-pollination in a controlled greenhouse environment in Muenster, Germany in 2012.

Asexual reproduction of the new *Lantana* plant by terminal cuttings in a controlled greenhouse environment in Muenster, Germany since 2013 has shown that the unique features of this new *Lantana* plant are stable and reproduced true to type in successive generations.

SUMMARY OF THE INVENTION

Plants of the new *Lantana* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'VOLLAN 1317'. These characteristics in combination distinguish 'VOLLAN 1317' as a new and distinct *Lantana* plant:

1. Compact, upright to outwardly spreading plant habit.
2. Freely branching growth habit; dense and bushy plant form.
3. Early and freely flowering habit.
4. Flowers that are initially yellow in color and with development become orange and red in color.
5. Good garden performance.

Plants of the new *Lantana* can be compared to plants of the female parent selection. Plants of the new *Lantana* differ primarily from plants of the female parent selection in the following characteristics:

1. Plants of the new *Lantana* are more compact than plants of the female parent selection.
2. Plants of the new *Lantana* are not as vigorous as plants of the female parent selection.
3. Plants of the new *Lantana* and the female parent selection differ in flower color as plants of the female parent selection have flowers that are orange in color.

Plants of the new *Lantana* can be compared to plants of the *Lantana camara* 'Flortanapi', disclosed in U.S. Plant Pat. No. 24,555. In side-by-side comparisons, plants of the new *Lantana* differ from plants of 'Flortanapi' in the following characteristics:

1. Plants of the new *Lantana* are larger and more vigorous than plants of 'Flortanapi'.
2. Plants of the new *Lantana* are more freely branching than plants of 'Flortanapi'.
3. Plants of the new *Lantana* have larger inflorescences with more flowers per inflorescence than plants of 'Flortanapi'.
4. Plants of the new *Lantana* and 'Flortanapi' differ in flower color and flowers of plants of 'Flortanapi' are red purple, red orange and yellow orange in color.

BRIEF DESCRIPTION OF THE PHOTOGRAPH

The accompanying colored photograph illustrates the overall appearance of the new *Lantana* plant showing the colors as true as it is reasonably possible to obtain in colored reproductions of this type. Colors in the photograph may differ slightly from the color values cited in the detailed botanical description which accurately describe the colors of the new *Lantana* plant.

The photograph is a side perspective view of a typical flowering plant of 'VOLLAN 1317' grown in a container.

DETAILED BOTANICAL DESCRIPTION

The aforementioned photograph and following observations and measurements describe plants grown during the spring in 12-cm containers in a glass-covered greenhouse in Muenster, Germany and under commercial practices typical of commercial *Lantana* production. During the production of the plants, day temperatures ranged from 18° C. to 25° C., night temperatures ranged from 15° C. to 18° C. and light levels ranged from 5 to 65 klux. Plants were pinched two to three weeks after planting and were six months old when the photograph and the description were taken. In the following description, color references are made to The Royal Horticultural Society Colour Chart, Sixth Edition, except where general terms of ordinary dictionary significance are used.

Botanical classification: *Lantana camara* 'VOLLAN 1317'.

Parentage:

*Female, or seed, parent*.—Unnamed proprietary selection of *Lantana camara*, not patented.

*Male, or pollen, parent*.—Unknown selection of *Lantana camara*, not patented.

Propagation:

*Type*.—By terminal cuttings.

*Time to initiate roots, summer*.—About one to two weeks at temperatures ranging from about 20° C. to 25° C.

*Time to initiate roots, winter*.—About two to three weeks at temperatures ranging from about 15° C. to 23° C.

*Time to produce a rooted young plant, summer*.—About three weeks at temperatures ranging from about 20° C. to 25° C.

*Time to produce a rooted young plant, winter*.—About 30 days at temperatures ranging from about 15° C. to 23° C.

*Root description*.—Fibrous; fine in thickness.

*Rooting habit*.—Freely branching; medium density.

Plant description:

*Plant and growth habit*.—Compact, upright to outwardly spreading plant habit; moderately vigorous growth habit and moderate growth rate.

*Plant height*.—About 21 cm.

*Plant diameter*.—About 30 cm to 55 cm.

Lateral branch description:

*Branching habit*.—Freely branching habit with about five primary lateral branches developing per plant; each primary lateral branch with potentially two secondary lateral branches developing at every node; pinching enhances lateral branch development.

*Length*.—About 19 cm to 30 cm.

*Diameter*.—About 4 mm to 6 mm.

*Internode length*.—About 1.8 cm to 4 cm.

*Strength*.—Strong.

*Texture*.—Pubescent; rough, coarse; longitudinally ridged; woody towards the base.

*Color, developing stems*.—Close to 143B.

*Color, developed stems*.—Close to 199B to 199C.

Leaf description:

*Arrangement*.—Opposite, simple,

*Length*.—About 2 cm to 8.5 cm.

*Width*.—About 1 cm to 4 cm.

*Shape*.—Oval.

*Apex*.—Acute.

*Base*.—Obtuse.

*Margin*.—Serrate.

*Texture and luster, upper surface*.—Smooth, glabrous; somewhat leathery; matte.

*Texture, lower surface*.—Pubescent; rough; matte.

*Venation pattern*.—Pinnate; arcuate to reticulate.

*Color*.—Developing leaves, upper and lower surfaces: Close to 144A. Fully expanded leaves, upper surface: Close to 136A; venation, close to 144A. Fully expanded leaves, lower surface: Close to 137A; venation, close to 138D.

*Petiole length*.—About 2 cm.

*Petiole diameter*.—About 1.5 mm.

*Petiole texture, upper and lower surfaces*.—Pubescent, hairs minute; coarse.

*Petiole color, upper and lower surfaces*.—Close to 141D.

Flower description:

*Flower arrangement and flowering habit*.—Solitary tubular to somewhat salverform flowers arranged in terminal and axillary hemispherical umbels; flowers face mostly upward or outward; freely flowering habit with about 50 flowers developing per inflorescence and numerous inflorescences developing per plant during the flowering season.

*Natural flowering season*.—Early flowering habit, plants begin flowering about 10 to 16 weeks after planting; long flowering period, plants of the new *Lantana* flower continuously from spring to autumn in Germany.

*Flower longevity on the plant*.—About 7 to 10 days; flowers not persistent.

*Fragrance*.—Strongly fragrant; spicy.

*Inflorescence height*.—About 3.5 cm.

*Inflorescence diameter*.—About 5 cm.

*Flowers*.—Appearance: Flared trumpet, corolla fused, four-parted; flowers are sessile. Diameter: About 8 mm to 10 mm. Depth (height): About 1.5 cm to 2 cm. Throat diameter: About 2 cm. Tube length: About 1 cm. Tube diameter: About 1.5 mm.

*Flower buds*.—Length: About 8 mm. Diameter: About 3 mm. Shape: Tubular. Color: Close to 145A.

*Corolla*.—Arrangement: Single whorl of four fused petals. Petal lobe length: About 5 mm. Petal lobe width: About 7 mm. Petal lobe shape: Obovate. Petal lobe apex: Obtuse. Petal margin: Entire, ruffled. Petal texture, upper surface: Smooth, glabrous. Petal texture, lower surface: Pubescent. Throat and tube texture: Pubescent. Color: When opening, upper surface: Close to 3A; with development, becoming closer to 12A and N25B. When opening, lower surface: Close to 3C; with development, becoming closer to 12D. Fully opened, upper surface: Close to N25A and 34B; color does not change with development. Fully opened, lower surface: Close to 12D; color does not change with development. Throat and tube: Close to 1B.

*Calyx*.—Appearance: Tubular calyx with four fused sepals. Length: About 5 mm. Diameter: About 1 mm.

Sepal apex: Broadly acute. Sepal margin: Entire. Sepal texture, inner and outer surfaces: Pubescent. Sepal color, inner and outer surfaces: Close to 135B.

*Peduncles*.—Length: About 3.5 cm. Diameter: About 1.5 mm. Strength: Strong. Texture: Pubescent, rough. Color: Close to 143B.

*Reproductive organs*.—Stamens: Quantity and arrangement: Four per flower, adnate to floral tube. Filament length: Less than 1 mm. Filament color: Close to 1D. Anther length: About 1 mm. Anther shape: Ovoid, bi-lobed. Anther color: Close to 162A. Pollen amount: Moderate. Pollen color: Close to 162A. Pistils: Quantity: One per flower. Pistil length: About 3 mm. Stigma shape: Funnel-shaped. Stigma color: Close to 145B. Style length: About 2 mm. Style color: Close to 145D. Ovary color: Close to 145D. Fruits and seeds: Fruit and seed development have not been observed on plants of the new *Lantana*.

Garden performance: Plants of the new *Lantana* have been observed to have good garden performance and to tolerate wind, rain and temperatures ranging from about 4° C. to about 33° C.

Pathogen & pest tolerance: Plants of the new *Lantana* have not been observed to be tolerant to pathogens and pests common to *Lantana* plants.

It is claimed:

1. A new and distinct *Lantana* plant named 'VOLLAN 1317' as illustrated and described.

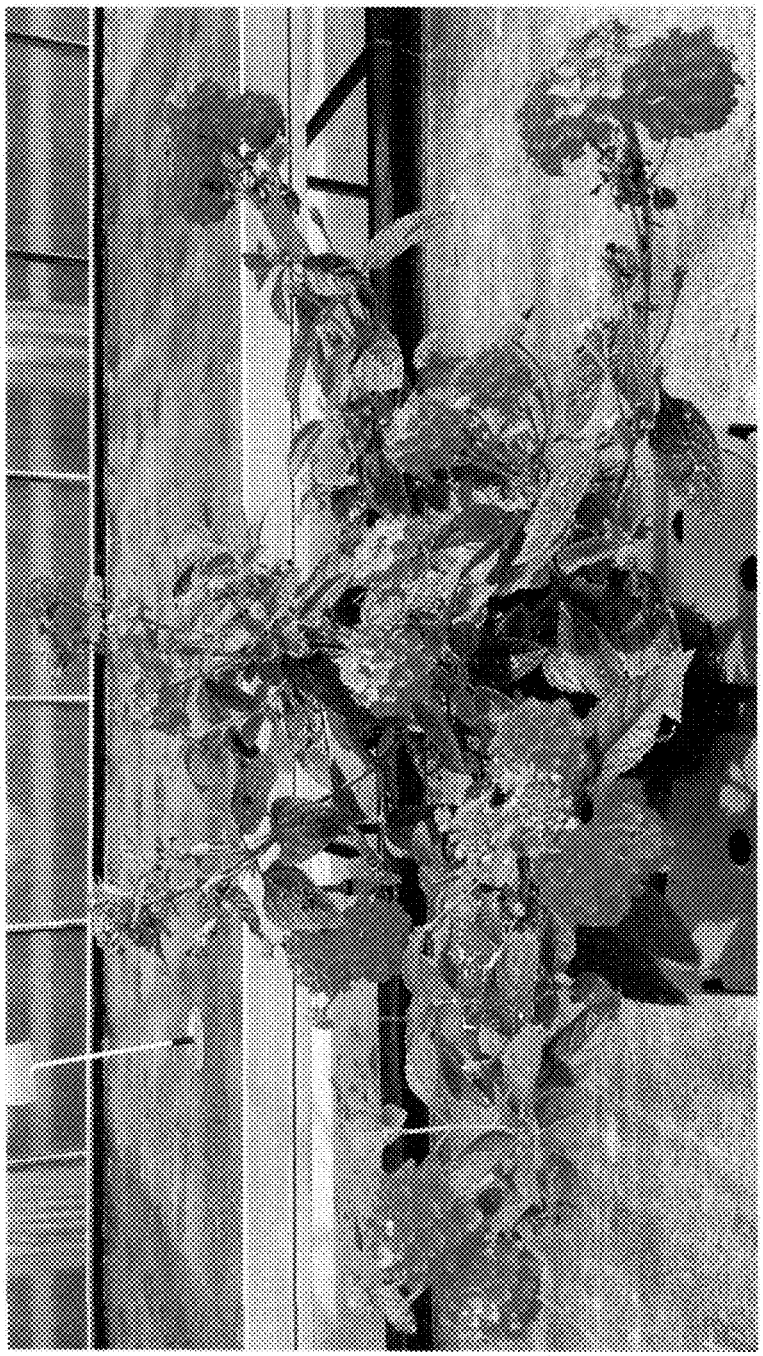

* * * * *